US012733900B2

(12) United States Patent
Debes et al.

(10) Patent No.: US 12,733,900 B2
(45) Date of Patent: Sep. 15, 2026

(54) METHOD AND SYSTEM USING ULTRASOUND REFLECTIONS OF MAIN PORTAL VEIN TO PREDICT LIVER CANCER

(71) Applicant: Regents of the University of Minnesota, Minneapolis, MN (US)

(72) Inventors: Jose D. Debes, Minneapolis, MN (US); Ju Sun, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 18/924,434

(22) Filed: Oct. 23, 2024

(65) Prior Publication Data

US 2025/0134491 A1 May 1, 2025

Related U.S. Application Data

(60) Provisional application No. 63/593,079, filed on Oct. 25, 2023.

(51) Int. Cl.
*A61B 8/14* (2006.01)
*A61B 8/00* (2006.01)
*A61B 8/06* (2006.01)
*A61B 8/08* (2006.01)

(52) U.S. Cl.
CPC ................ *A61B 8/085* (2013.01); *A61B 8/06* (2013.01); *A61B 8/48* (2013.01)

(58) Field of Classification Search
CPC .. A61B 8/06; A61B 8/085; A61B 8/48; A61B 8/488; A61B 8/5223
See application file for complete search history.

(56) References Cited

U.S. PATENT DOCUMENTS

2013/0023767 A1* 1/2013 Mammone .............. A61B 8/14 600/443

* cited by examiner

*Primary Examiner* — Mark D Remaly
(74) *Attorney, Agent, or Firm* — Theodore M. Magee; Westman, Champlin & Koehler, P.A.

(57) ABSTRACT

A method includes sensing sound reflections from a living body and determining frequency intensities in the sound reflections at each of a sequence of time windows. The frequency intensities are then used to predict the presence of liver cancer.

7 Claims, 3 Drawing Sheets

METHOD AND SYSTEM USING ULTRASOUND REFLECTIONS OF MAIN PORTAL VEIN TO PREDICT LIVER CANCER

CROSS-REFERENCE TO RELATED APPLICATION

The present application is based on and claims the benefit of U.S. provisional patent application Ser. No. 63/593,079, filed Oct. 25, 2023, the content of which is hereby incorporated by reference in its entirety.

BACKGROUND

Hepatocellular carcinoma (HCC) is the third leading cause of cancer-related death worldwide. Currently, ultrasounds of the liver are used to detect the presence of cancerous masses on the liver. However, such ultrasounds require skilled operators who must examine the entire liver. Using such ultrasounds, large numbers of liver cancers remain undetected, especially at early stages of the cancer.

The discussion above is merely provided for general background information and is not intended to be used as an aid in determining the scope of the claimed subject matter. The claimed subject matter is not limited to implementations that solve any or all disadvantages noted in the background.

SUMMARY

A method includes sensing sound reflections from a living body and determining frequency intensities in the sound reflections at each of a sequence of time windows. The frequency intensities are then used to predict liver cancer.

In accordance with a further embodiment, a sonography system includes a transducer, receiving sound signals from a living body and converting the sound signals into electrical signals and a transform module for transforming the electrical signal into frequency intensity values. A neural network receives a representation of the frequency intensity values as input and outputs an indication of whether the living body has liver cancer. A display displays whether the living body has liver cancer.

In accordance with a still further embodiment, a method includes generating an image based on blood flow and using the image to predict liver cancer.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

The present embodiments provided an improved method and system for detecting liver cancers such as hepatocellular carcinoma. In accordance with the present embodiments, ultrasound reflections of the blood flow carried by the main portal vein are provided as input to a neural network, which uses the reflections to predict whether the patient has liver cancer. This eliminates the search for a cancerous mass. In accordance with one embodiment, the ultrasound reflections are converted into a graph and an image of the graph is provided to the neural network as input.

Figure 1:
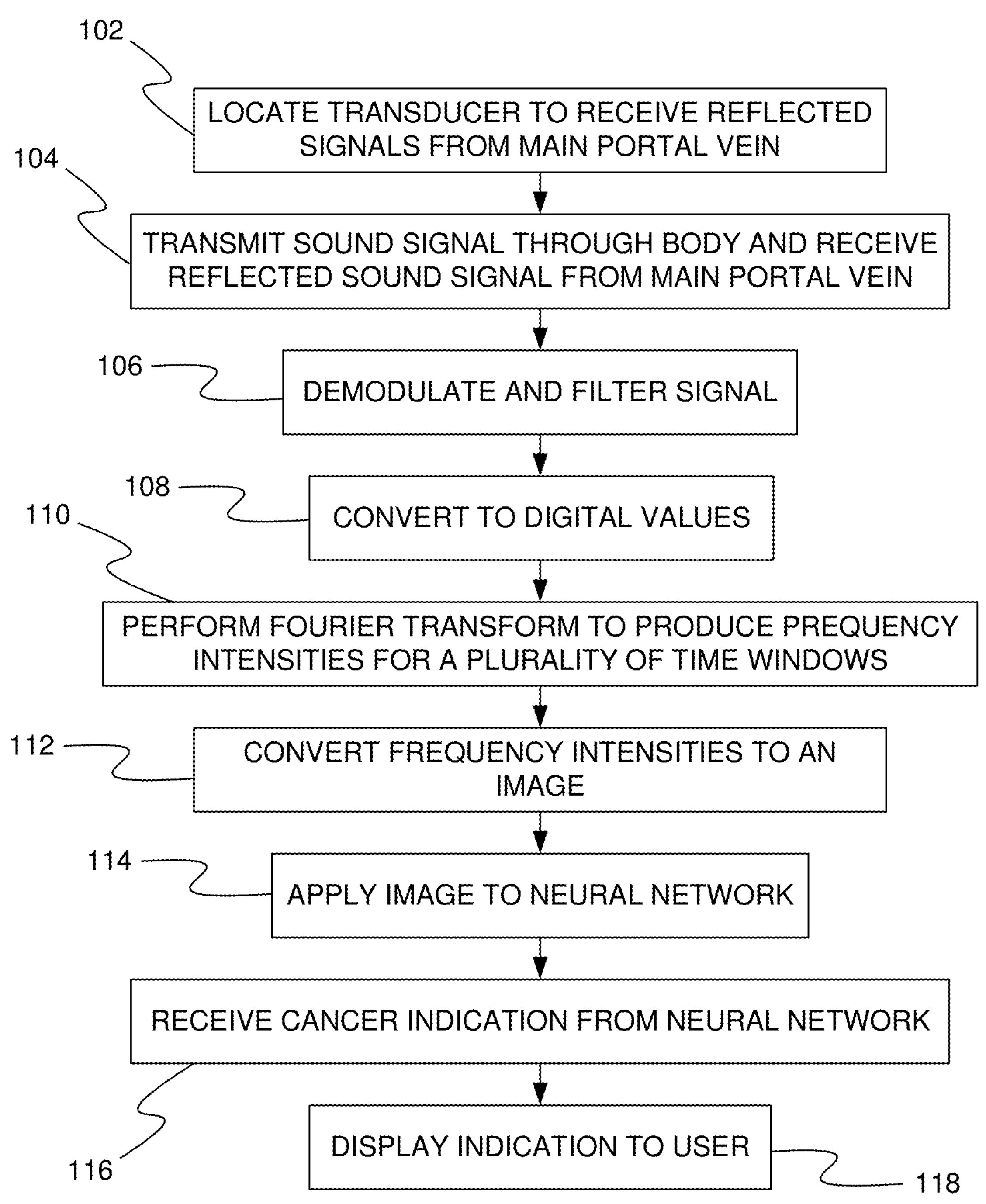
FIG. 1 is a flow diagram of a method of detecting liver cancer.
Figure 2:
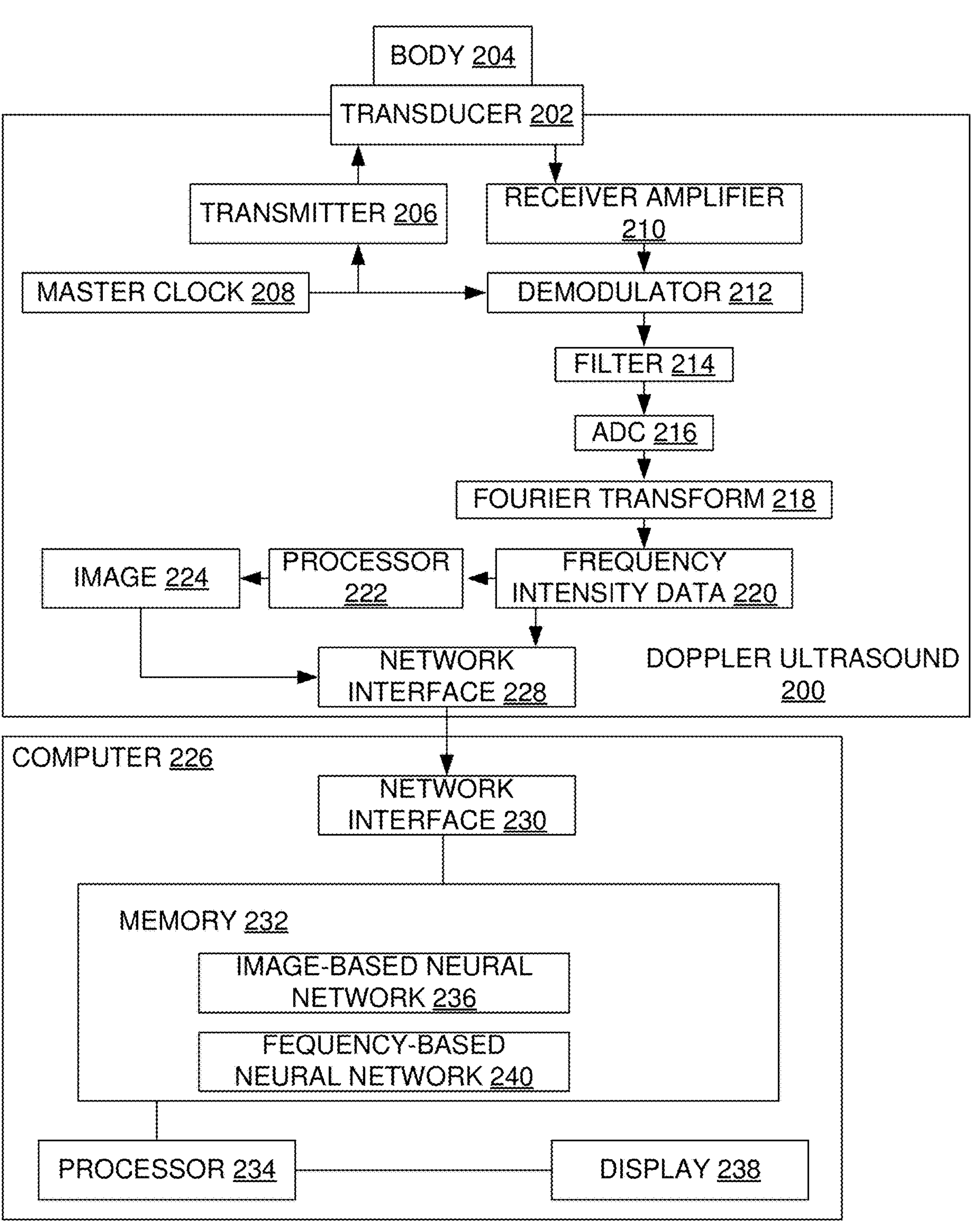
FIG. 2 is a block diagram of a sonography system for detecting liver cancer.

FIG. 1 provides a flow diagram of a method of detecting liver cancer and FIG. 2 provides a block diagram of a sonography system for detecting liver cancer.

In step 102 of FIG. 1, a transducer 202 of a doppler ultrasound system 200 is placed externally on a living body 204 so that a sound signal generated by transducer 202 is reflected by the main portal vein in living body 204. In particular, transducer 202 is positioned such that the sound signals are reflected by cells moving in the blood flow carried by the main portal vein.

At step 104, a transmitter 206 in doppler ultrasound system 200 generates a periodic electrical signal with a frequency that is based on the frequency of a clock signal generated by master clock 208. This electrical signal causes transducer 202 to output a sound signal with the same frequency. This sound signal travels through body 204 and is reflected by the cells in the blood flow carried by the main portal vein. The sound reflections from the cells travel back through body 204 and are converted by transducer 202 into an electrical signal.

When the sound signal is reflected by blood flow, the velocity of the flow relative to transducer 202 causes the reflected sound to be frequency shifted relative to the input sound signal. Since different cells are traveling at different velocities within the main portal vein, the total reflected signal received by transducer 202 covers a broad spectrum of frequencies with the intensity of any one frequency being dependent on the number of cells that are moving with a particular velocity. Thus, the frequencies in the reflected sound signal represent different velocities of blood in the main portal vein and the intensities of those frequencies represent the number of cells moving with those velocities. Similarly, the frequencies of the electrical signal output by transducer 202 also represent the velocities of cells in the main portal vein with the magnitudes of those frequencies representing the number of cells with those velocities.

The electrical signal produced by transducer 202 is amplified by a receiver amplifier 210 and the amplified signal is demodulated by demodulator 212 at step 106. During demodulation, the component of the amplified signal associated with the frequency of the master clock is removed from the signal. The demodulated signal is further filtered by a filter 214 to remove higher harmonics of the master clock to produce a filtered signal.

At step 108, the filtered signal is converted into a sequence of digital values using an analog-to-digital convertor 216. At step 110, the sequence of digital values is converted to the frequency domain using a Fourier transform 218 such as a Fast Fourier Transform. This produces intensity values 220 for a set of frequencies at a sequence of time windows.

Figure 3:
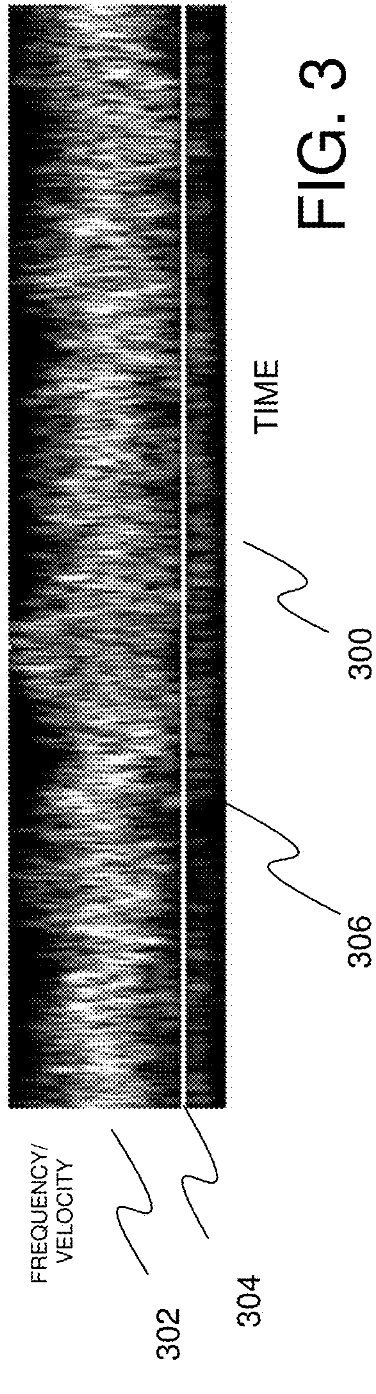
FIG. 3 is an example of an image used as input to a neural network for detecting liver cancer.

At step 112, frequency intensity data 220 is used by a processor 222 to form image 224, which is a pictorial representation of the frequency intensity data. In accordance with one embodiment, the pictorial representation is a graph, like graph 300 shown in FIG. 3, with time along horizontal axis 300 and frequency/velocity along vertical axis 302. Horizontal line 304 represents the frequency of master clock 208, with frequency values above line 304 representing cells traveling toward transducer 202 and frequency values below line 304 representing cells traveling away from transducer 202. Each time window is represented by a vertical line such as vertical line 306, which represents the frequencies present in the time window. The intensity of each frequency is represented by the brightness of the line at the vertical position that represents the frequency. Thus, portions of the line that are brighter represent higher intensity frequencies, which in turn represents a higher number of cells moving with the velocity associated with that frequency.

Image 224 is provided to a computer 226 through network interface 228 of doppler ultrasound system 200 and network interface 230 of computer 226. Such network interfaces can include cable connections, WiFi connections and short-range connections such as Bluetooth. Image 224 is stored in a memory 232 of computer 226. A processor 234 executes an image-based neural network 236 stored in memory 232. During execution of image-based neural network 236, processor 234 applies image 224 as input to the neural network at step 114. Using image 224 as input, neural network 236 generates a prediction as to whether the patient has liver cancer.

In accordance with one embodiment, neural network 236 is a convolution neural network trained on images generated from ultrasounds of patients with and without liver cancer.

At step 116, an indication of whether the patient has liver cancer is received from the execution of neural network 236. At step 118, processor 234 displays the indication provided by neural network 236 on a display 238.

In an alternative embodiment, frequency intensity data 220 is provided to computer 226 instead of image 224. Processor 234 then executes a frequency-based neural network 240 stored in memory 232. During execution of frequency-based neural network 240, processor 234 applies frequency intensity data 220 as input and frequency-based neural network 240 generates a prediction as to whether the patient has liver cancer. Processor 234 then displays the prediction on display 238.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms for implementing the claims.

What is claimed is:

1. A sonography system comprising:

a transducer, receiving sound signals from a living body and converting the sound signals into electrical signals;

a transform module for transforming the electrical signal into frequency intensity values;

a neural network receiving a representation of the frequency intensity values as input and outputting an indication of whether the living body has liver cancer, wherein the representation of the frequency intensity values comprises an intensity value for each of a set of frequencies at each of a set of time points over a period of time; and a display for displaying whether the living body has liver cancer.

2. The sonography system of claim 1 wherein the representation of the frequency intensity values comprises an image and wherein the sonography system further comprises a processor that converts the frequency intensity values into the image.

3. The sonography system of claim 2 wherein the image comprises a graph of frequency intensities over time.

4. The sonography system of claim 3 wherein the image uses brightness to indicate intensity.

5. The sonography system of claim 1 wherein the received sound signals comprise reflected ultrasound signals.

6. The sonography system of claim 5 wherein the reflected ultrasound signals are reflected from a main portal vein.

7. The sonography system of claim 6 wherein the reflected ultrasound signals are not reflected from the liver.

* * * * *